Figure 2:
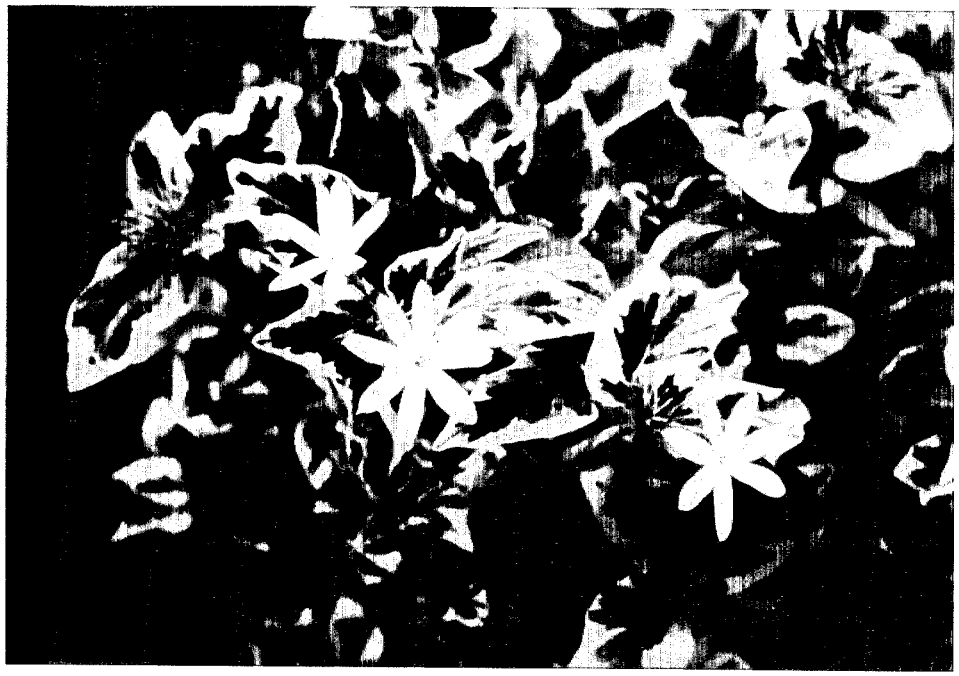

United States Patent [19]

Fisher

[11] Patent Number: Plant 7,719

[45] Date of Patent: Nov. 26, 1991

[54] *JASMINE MULTIFLORUM* 'TIFFANY'

[75] Inventor: Wesley C. Fisher, Sebring, Fla.

[73] Assignee: Hidden Acres Nursery Inc., Sebring, Fla.

[21] Appl. No.: 526,998

[22] Filed: May 17, 1990

[51] Int. Cl.[5] ..... A01H 5/00

[52] U.S. Cl. ..... Plt./54

[58] Field of Search ..... Plt./54

*Primary Examiner*—James R. Feyrer

*Attorney, Agent, or Firm*—Frank B. Robb

[57] ABSTRACT

A Jasmine plant of generally classic form and other characteristics, readily distinguishable however, by the extremely variegated leaves which have random patterns of yellow colors varying from simple border coloration to intricate designs, no two of which seem to be identical, though usually all leaves are variegated more or less extensively, and the plant has the usual white flowers of delicate fragrance when in bloom.

1 Drawing Sheet

BACKGROUND OF THE INVENTION

As the operator of a large nursery which produces many varieties of plants for all purposes, I have been careful to observe those which seem to be different from related and parent plants.

While it is not my intent to purposely breed new varieties or hybridize plants, since our nursery does produce large quantities of Jasmine plants, we constantly observe the growth of such plants.

It is thus realistic to expect that might be discovered, particularly when a plant is grown in very large numbers. However it is clearly unpredictable what magnitude and direction or which traits expressed might be changed in such an occurrence in any discovered sport. The plant of this disclosure was a spontaneous mutant which differed conspicuously from the parent plant by the dramatic color difference of its leaves which express a marginal variegation of characteristically unpredictable degree in extent and pattern.

In view of the fact that the characteristically limitless patterns appearing on the leaves of the instant variety are very noticeable and of such contrast with the usual green background of the *Jasminum multiflorum* leaf, the parent plant which appeared as a sport in a cultivated row of plants was immediately observed.

Careful asexual reproduction by cuttings of the plant has established that the variegations of one pattern or another continue to appear in successive generations and primarily at the borders of the leaves though not always limited to that area.

While the foliar variegations of the discovered plant do not follow any predictable pattern or degree, they have been faithfully observed to occur as predominantly marginal, and to be of the same color combinations in each of the asexually reproduced clones to establish that the variation and degree of variegation and widely varying pattern of variegation are characteristic and that the plant is stable.

The type of variegation described is seen in numerous other species with marginal leaf variegations. Light yellow coloration predominantly occurs along the margin of leaves in varied and uneven distances toward the center of each leaf blade. Normally continuous patterns of deep green occupy central leaf portions and appear to occupy at least the top mesophyll layer within each leaf. Shadings of lighter green occur in haphazard patterns between the deep green central portion and yellow marginal pattern which are apparently due to an absence of chlorophyll in at least the top layer of mesophyll cells within leaves. As first viewed from a distance, the pattern of variegation appears to comprise two colors, but close inspection reveals a deep, unmasked green that can be seen to dominate the central blade portion of the leaves, a yellow dominates the margins and an intermediate green masked by a yellow layer occurs in random locations between the solid yellow and deep green. The oldest leaves normally disclose a higher degree of yellow pattern by area.

This has resulted in increasing quantities of hardy plants being produced and the continued appearance of the random patterns on the leaves of a range of yellow color which I believe provide an attractive plant for decorative purposes.

As a tropical jasmine, my new variety does in fact produce vigorous, freely spreading, rather downy shrubs, generally usually having cordate dull green leaves, but in this instance considerably more noticeable because of the yellow variegations which appear and which provides an entirely different overall appearance.

The usual white flowers which are associated with small jasmine plants, also continue to appear and provide a further showy plant with delicate fragrance, which is not overwhelming but certainly distinctive of the *Jasminum multiflorum* and very much like that of the parent plant.

As a conmmercial plant my new variety continues to provide ground cover if so desired, a shrub when appropriately trimmed, and a plant which will wrap, a characteristic of this type of jasmine.

I have also found that my new variety is not attractive to insects which are harmful and is disease resistant as are other Jasminum Plants.

In the detailed description hereinafter set forth, the most distinguishing characteristics are noted, bearing in mind that other than the distinctions specifically described, my new variety more merely resembles the parent of which it is a sport.

The variegations are reminiscent of certain old time variations and designs and as such have caused me to select the designation of my new plant as 'Tiffany' for purposes of this description.

Figure 1:
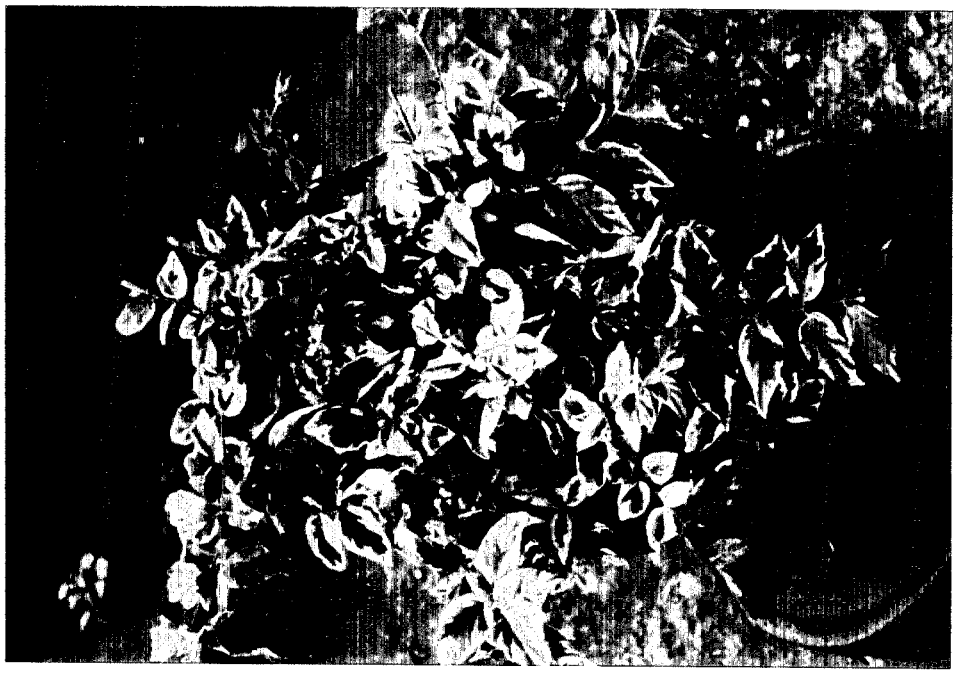

By way of illustration, there is provided a photo of a typical plant as it may appear generally, although no two plants are identical, which serves to illustrate the overall aspects of the plant in FIG. 1.

FIG. 2 shows a closeup of some of the foliage to disclose the random patterns of variegation which appear, the photos providing color illustrations as nearly like the actual plants as is possible to provide by photographic technique, with the color references related to the Munsell Color Cascade.

Parentage: Sport of *Jasminum multiflorum.*

Propagation: Asexual reproduction by cuttings at a nursery in the vicinity of Sebring, Fla.

Plant form: Shrub with slender branches. Finely pubescent.

*Color.*—Green with leaves having yellow margins and central green patterns of variegation.

*Lenticels.*—Few; small.

Leaves:

*Length.*—3.5 cm.

Width.—1.5–3.0 cm.

*Size.*—Medium; thin; smooth.

*Form.*—Ovate; tip broadly accuminate base rounded to truncate

*Color.*—Variegated, green and yellow ranging from 27-3 to 21-15.

*Margin.*—Wavy throughout.

*Petiole.*—Short; slender; pubescent.

Flower buds: Tender; small; long; pointed; free; smooth. Pedicels pubsecent.

Flowers:

*Date first and full bloom.*—Year around.

*Size.*—Medium.

*Color.*—White.

Does not produce fruit.

I claim:

1. A new and distinctive variety of *Jasminum multiflorum* substantially as shown and described herein, characterized particularly as to novelty by the random pattern of contrasting yellow colors as variegations on the green leaves, with hardy, profuse production, other characteristics being typical of *Jasminum multiflorum* including pubescence, and delicate fragrance of the flowers which are white.

* * * * *